United States Patent
Kobayashi

(10) Patent No.: US 7,348,290 B2
(45) Date of Patent: Mar. 25, 2008

(54) ARENE-RUTHENIUM COMPLEXES IMMOBILIZED ON POLYMERS, CATALYSTS CONSISTING OF THE COMPLEXES, AND PROCESSES FOR ORGANIC SYNTHESES WITH THE SAME

(75) Inventor: Shu Kobayashi, Tokyo (JP)

(73) Assignee: Japan Science and Technology Agency, Saitama (JP)

( * ) Notice: Subject to any disclaimer, the term of this patent is extended or adjusted under 35 U.S.C. 154(b) by 377 days.

(21) Appl. No.: 10/507,073

(22) PCT Filed: Mar. 11, 2003

(86) PCT No.: PCT/JP03/02861

§ 371 (c)(1),
(2), (4) Date: Nov. 3, 2004

(87) PCT Pub. No.: WO03/076478

PCT Pub. Date: Sep. 18, 2003

(65) Prior Publication Data

US 2005/0119416 A1    Jun. 2, 2005

(30) Foreign Application Priority Data

Mar. 11, 2002    (JP)    ............... 2002-065662

(51) Int. Cl.
*B01J 27/185*    (2006.01)
(52) U.S. Cl. ............. 502/213; 525/326.1; 556/16
(58) Field of Classification Search ............. 525/326.1; 556/16; 502/213
See application file for complete search history.

(56) References Cited

U.S. PATENT DOCUMENTS 5,981,782 A * 11/1999 Okeda et al. ............... 556/23

FOREIGN PATENT DOCUMENTS

| JP | 56-118404 | 9/1981 |
|---|---|---|
| JP | 57-47304 | 3/1982 |
| WO | WO 01/36660 | 5/2001 |
| WO | WO 02/076920 | 10/2002 |

OTHER PUBLICATIONS

Akiyama et al., 2002, Angew. Chem. Int. Ed, 2002, 41(14): 2602-2604.*
Noels, 2000, CAS: 132:79002.*
Jan et al., 2000, CAS: 133:350569.*
Noels, 2000, EP 0970972.*
Ryo Akiyama et al., "A Novel Polymer-Supported Arene-Ruthenium Complex for Ring-Closing Olefin Metathesis," *Angew. Chem. Int. Ed.*, vol. 41, No. 14, pp. 2602-2604 (2002).

* cited by examiner

*Primary Examiner*—Rei-tsang Shiao
(74) *Attorney, Agent, or Firm*—Wenderoth, Lind & Ponack, L.L.P.

(57) ABSTRACT

A novel polymer-supported arene-ruthenium complex represented by the following formula:

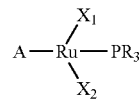

, wherein A represents an organic polymer with a side chain containing an aromatic ring coordinated to Ru, $X_1$ and $X_2$ represent the same or different halogen atoms, and R represents a hydrocarbon group that may have a substituent is provided for use as a catalyst. This novel polymer-supported arene-ruthenium complex and catalyst thereof can be produced by a simple process, are stable and easy to recover, have a high catalytic activity, and can be used for various organic synthesis reactions. Novel methods for an organic synthesis reaction such as ring-opening metathesis reaction of an olefin compound and reduction of a carbonyl group, using the catalyst are provided.

12 Claims, No Drawings

ARENE-RUTHENIUM COMPLEXES IMMOBILIZED ON POLYMERS, CATALYSTS CONSISTING OF THE COMPLEXES, AND PROCESSES FOR ORGANIC SYNTHESES WITH THE SAME

This application is a 371 of PCT/JP03/02861 filed on Mar. 11, 2003.

TECHNICAL FIELD

The present invention relates to a polymer-supported arene-ruthenium complex, a catalyst thereof, and organic synthesis methods using the same.

BACKGROUND ART

It has been known that arene-ruthenium complexes with aromatic rings coordinated to Ru are usable as catalyst precursors for various organic synthesis reactions. However, the reaction catalysts prepared from the arene-ruthenium complexes are disadvantageous in that they are deteriorated by contact with air or moisture and that it is often difficult to recover them.

Catalysts supported on polymers have been studied to overcome these disadvantages. However, practical methods of supporting the catalyst on the polymer have not been established, and experimental polymer-supported catalysts have outstanding serious disadvantages of low catalytic activity and limitation on reactions to which the catalyst can be applied.

Accordingly, an object of the present invention is to fundamentally overcome the above problems, thereby providing a novel polymer-supported arene-ruthenium complex and a catalyst thereof, which can be produced by a simple process, are stable and easy to recover, have a high catalytic activity, and can be used for various organic synthesis reactions, and novel methods using the same for an organic synthesis reactions such as ring-closing metathesis of an olefin compound and reduction of a carbonyl group.

DISCLOSURE OF THE INVENTION

To solve the above problems, according to a first aspect of the present invention, there is provided a polymer-supported arene-ruthenium complex characterized in that the complex is represented by the following formula:

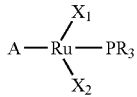

wherein A represents an organic polymer with a side chain comprising an aromatic ring coordinated to Ru, $X_1$ and $X_2$ represent the same or different halogen atoms, and R represents a hydrocarbon group that may have a substituent.

According to a second aspect of the invention, there is provided the polymer-supported arene-ruthenium complex characterized in that the hydrocarbon group is an alicyclic hydrocarbon group or an aromatic hydrocarbon group. According to a third aspect, there is provided the polymer-supported arene-ruthenium complex characterized in that the aromatic ring of the side chain is a benzene ring. According to a fourth aspect, there is provided the polymer-supported arene-ruthenium complex characterized in that the organic polymer is a polystyrene.

Further, according to a fifth aspect of the invention, there is provided a method for producing the polymer-supported arene-ruthenium complex of any one of the first to fourth aspects of the invention, characterized by comprising a ligand exchange reaction of a complex monomer represented by the following formula:

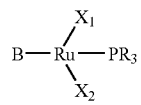

wherein B represents an aromatic compound comprising an aromatic ring coordinated to Ru, and $X_1$, $X_2$ and R are as defined above, with the organic polymer A that has an aromatic ring at a side chain.

Furthermore, according to a sixth aspect of the invention, there is provided a polymer-supported arene-ruthenium catalyst for an organic synthesis reaction, characterized by comprising the polymer-supported arene-ruthenium complex of any one of the first to fourth aspects of the invention as an active component. According to a seventh aspect, there is provided the polymer-supported arene-ruthenium catalyst characterized in that the catalyst is prepared by mixing the complex with a phosphine compound. According to an eighth aspect, there is provided the polymer-supported arene-ruthenium catalyst characterized in that the catalyst is prepared by mixing the complex with $MPF_6$ in which M represents a monovalent cation. According to a ninth aspect, there is provided the polymer-supported arene-ruthenium catalyst characterized in that the catalyst is prepared by mixing the complex with an alkynyl alcohol compound.

According to a tenth aspect of the invention, there is provided a method of an organic synthesis reaction, characterized in that a ring-closing metathesis reaction of an olefin compound is carried out in the presence of the catalyst of any one of the sixth to ninth aspects of the invention. According to an eleventh aspect, there is provided a method of an organic synthesis reaction, characterized in that reduction of a carbonyl group is carried out in the presence of the catalyst of the sixth or seventh aspect of the invention to synthesize an alcohol compound. According to a twelfth aspect, there is provided a method of an organic synthesis reaction, characterized in that a reaction comprising carbon-carbon addition of an acetylene group is carried out in the presence of the catalyst of any one of the sixth to eighth aspects of the invention.

BEST MODE FOR CARRYING OUT THE INVENTION

The present invention is characterized by the above aspects. An embodiment of the invention is described below.

The polymer-supported arene-ruthenium complex provided in the invention is represented by the above general formula. The aromatic ring in the side chain of the organic polymer A is coordinated to the Ru (ruthenium), and the halogen atoms $X_1$ and $X_2$, and the phosphine group $PR_3$ are bonded to the Ru. In this structure, R forming the phosphine group is a hydrocarbon group that may have a substituent, and the hydrocarbon group may be an aliphatic, alicyclic, aromatic, or heterocyclic group. The hydrocarbon group is preferably an alicyclic hydrocarbon group such as a cyclohexyl group and a cyclopentyl group, or an aromatic hydrocarbon group such as a phenyl group. The hydrocarbon group may have a substituent as long as the substituent does not inhibit the immobilization on the polymer and the activity of the catalyst. Examples of the substituents include hydrocarbon groups such as a methyl group, an ethyl group, a butyl group, and aryl groups, alkoxy groups, halogen atoms, ester groups, etc.

The hydrocarbon groups R's forming the phosphine group $PR_3$ may be the same or different groups selected from the above groups.

The halogen atoms $X_1$ and $X_2$ may be a chlorine atom, a bromine atom, an iodine atom, etc. respectively, and may be the same or different atoms.

The organic polymer A with the side chain containing the aromatic ring coordinated to the Ru (ruthenium) is not particularly restricted in its kind, and it is preferable that the aromatic ring in the side chain is a benzene ring. Typical examples of such organic polymers include polystyrenes, common and easily available. As a matter of course, the main chain of the polymer may contain not only a carbon chain but also an ether bond, an ester bond and additionally an amino bond, an amide bond, etc. as appropriate.

The polymer-supported arene-ruthenium complex of the invention can be, for instance, produced by the above-described ligand exchange reaction between the complex monomer and the organic polymer A. More practically, the ligand exchange reaction is preferably carried out in accordance with a microencapsulation method, which also is proposed by the inventors.

For example, in the production of a $RuCl_2(PPh_3)$ complex coordinated with and supported by the organic polymer polystyrene, a polymer-supported $PS-RuCl_2(PPh_3)$ complex can be produced by reacting a monomer complex in a cyclohexane solvent as shown in the following formula.

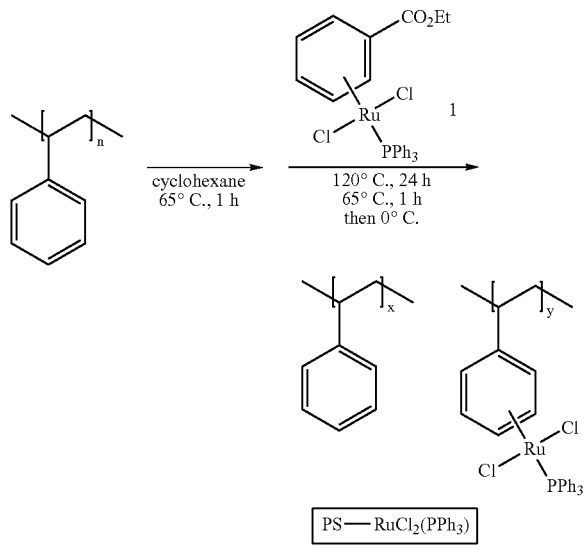

The polymer-supported arene-ruthenium complex of the invention can be effectively used for various organic synthesis reactions as a catalyst without modification or as a catalyst composition prepared by mixing with an auxiliary active component, a cocatalyst, can be used in a reaction accelerator, or can be accelerated by heating. The complex shows a high catalytic activity, and can be reused because it is polymer-supported, and expresses high catalytic activity in reutilization.

Thus, the catalyst or the prepared catalyst composition comprises the polymer-supported arene-ruthenium complex as an active component. The catalyst composition is a preparation mixed with a phosphine compound, or $MPF_6$ (in which M represents a monovalent cation), or an alcohol compound, an amine compound, an alkene compound, an alkynylene compound, etc.

As an organic synthesis reaction, a ring-closing metathesis reaction of an olefin compound is particularly useful. This reaction is such that a compound having at least two olefin bonds is closed into a ring, and can be one of important principal elementary reactions for synthesizing various pharmaceuticals, agricultural chemicals, perfumes, cosmetics, polymer materials, etc.

Examples of the catalysts effective for the ring-closing metathesis reaction include compositions of the polymer-supported arene-ruthenium complex and a phosphine compound, an alkynyl alcohol compound having an acetylene bond, $NaPF_6$, etc. In the preparation of the catalyst, various solvents may be used. Examples of the solvents include polar solvents such as alcohols, halogenated hydrocarbons, nitrites, amides, and sulfoxides, and hydrocarbons such as benzene, toluene, and hexane. Among these, preferred solvents include polar solvents such as mixed solvents of an alcohol and a hydrocarbon.

As a matter of course, the catalyst may be prepared before the organic synthesis reaction using the catalyst. Alternatively, the catalyst may be prepared by adding the components of the catalyst to the reaction system.

The catalyst is useful for various organic synthesis reactions, and has a high activity and excellent reusability.

For example, as described below in Examples, a ring-closing metathesis reaction shown in the following reaction formula can be achieved with remarkably excellent results by using the catalyst, and thus a 5-membered heterocyclic compound can be synthesized with a yield of 75% by the first use of the catalyst, with a yield of 81% by the second use of the catalyst, with a yield of 98% by the third use of the catalyst.

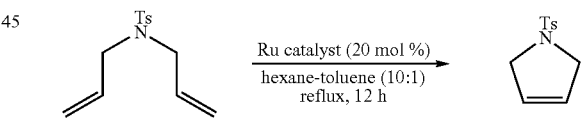

Further, the polymer-supported arene-ruthenium complex of the invention can form a reusable catalyst, which shows a high activity in alcohol synthesis by reducing a carbonyl group, a carbon-carbon addition of an acetylene group, etc.

The invention will be explained in more detail referring to Examples below which of course do not restrict the invention.

EXAMPLES

Example 1

Production of Polymer-Supported Arene-Ruthenium Complexes

Polymer-supported arene-ruthenium complexes (3a) and (3b) were produced in accordance with the following reaction formula.

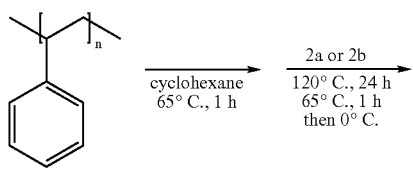

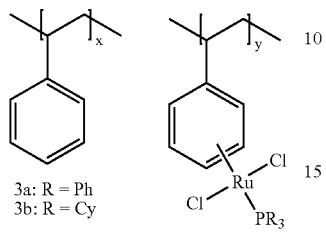

3a: R = Ph
3b: R = Cy (1) Synthesis of [Ru($\eta^6$-C$_6$H$_5$CO$_2$Et)($\eta^1$-PPh$_3$)Cl$_2$](2a)

Triphenylphosphine (0.321 g, 1.22 mmol) was added to 14.5 ml of a dichloromethane solution of a ruthenium dimer (1): [Ru($\eta^6$-C$_6$H$_5$CO$_2$Et)Cl$_2$]$_2$ (0.394 g, 0.61 mmol), and stirred at the room temperature for 30 minutes.

Ethanol was added thereto to generate precipitates, whereby a ruthenium complex (2a) was quantitatively obtained as the precipitates (0.715 g, 1.22 mmol).

Analytical characteristic values of the product are as follows.

TABLE 1

[Ru($\eta^6$-C$_6$H$_5$CO$_2$Et)($\eta^1$-PPh$_3$)Cl$_2$](2a) $^1$H NMR $\delta$=1.41(t, 3H, J=7.1Hz), 4.43(q, 2H, J=7.1Hz), 5.08(t, 2H, J=5.9Hz), 5.28-5.33(m, 1H), 6.44(d, 2H, J=6.1Hz), 7.35-7.50(m, 9H), 7.70-7.90(m, 6H); $^{13}$C NMR $\delta$=14.5, 62.6, 85.09, 85.11, 88.6, 95.31, 95.33, 128.1, 128.2, 130.59, 130.62, 132.5, 133.0, 134.1, 134.2, 163.8; $^{31}$P NMR $\delta$=25.8.

(2) Synthesis of [Ru($\eta^6$-C$_6$H$_5$CO$_2$Et)($\eta^1$-PCy$_3$)Cl$_2$] (2b)

A ruthenium complex (2b) was obtained in the same manner as (1) using tricyclohexylphosphine instead of triphenylphosphine.

(3) Synthesis of Polymer-Supported Arene-Ruthenium Complex (3a)

Polystyrene (5.00 g) was dissolved in cyclohexane (100 ml) at 65° C. The above ruthenium complex (2a) (0.20 g) was added to this solution, and stirred at 120° C. for 24 hours and at 65° C. for 1 hour.

The ligand exchange reaction process was monitored by a TLC. The ruthenium complex (2a) disappeared and ethyl benzoate was generated.

The reaction mixture was gradually cooled to 0° C., and phase separation was observed.

To the mixture was added hexane (100 ml) and it was left at room temperature for 12 hours. The resultant was washed with acetonitrile several times and dried at the room temperature for 24 hours, to obtain the polymer-supported arene-ruthenium complex PS-RuCl$_2$(PPh$_3$) (3a). It was confirmed by fluorescent X-ray analysis that 98% of the ruthenium metal was supported. The complex was identified by $^{31}$PSR-MAS NMR $\delta$=25.7 (PPh$^3$).

(4) Synthesis of Polymer-Supported Arene-Ruthenium Complex (3b)

The polymer-supported arene-ruthenium complex PS-RuCl$_2$(PCy$_3$) (3b) was obtained in the same manner as (3) using the complex (2b), $^{31}$PSR-MASNMR $\delta$=28.5 (PCy$_3$).

Example 2

Ring-Closing Metathesis Reaction (RCM)

A ring-closing metathesis reaction of N,N-diallyl-p-toluenesulfonamide (6) was carried out in accordance with the following reaction formula.

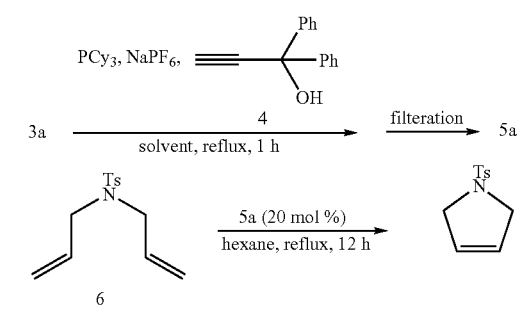

(1) Preparation of Catalyst

The polymer-supported arene-ruthenium complex PS-RuCl$_2$(PPh$_3$) (3a) (0.058 mmol/g, 689 mg, 0.04 mmol), tricyclohexylphosphine PCy$_3$ (11.2 mg, 0.04 mmol), 1,1-diphenyl-2-propynol (4) (8.3 mg, 0.04 mmol), and NaPF$_6$ (6.7 mg, 0.04 mmol) were added to a mixed solvent of isopropanol-hexane (1:10, 10 ml), and stirred under reflux for 1 hour.

Thus generated, the activated ruthenium catalyst (5a) was isolated by filtration, washed with ethanol and hexane, and then dried under a reduced pressure.

(2) Ring-Closing Metathesis Reaction 10 ml of a hexane-toluene (10:1) solution of N,N-diallyl-p-toluenesulfonamide (6) (50.3 mg, 0.20 mmol) was mixed with the activated ruthenium catalyst (5a) obtained in (1) at the room temperature, and then stirred under reflux for 12 hours.

The catalyst was isolated by filtration and washed with ethanol and hexane, and the filtrate was concentrated under a reduced pressure. It was confirmed by fluorescent X-ray analysis that ruthenium metal was not contained in the filtrate. The crude product was subjected to a silica gel chromatography, to obtain N-tosyl-2,5-dihydropyrrole (33.5 mg, 75% yield).

Characteristic values of the product are as follows.

TABLE 2

N-Tosyl-2,5-dihydropyrrole. $^1$H NMR $\delta$=2.43(s, 3H), 4.11(s, 4H), 5.65(s, 2H), 7.32(d, 2H, J=8.2Hz), 7.72(d, 2H, J=8.2Hz); $^{13}$C NMR $\delta$=21.4, 54.8, 125.4, 127.3, 129.7, 134.1, 143.4.

The recovered catalyst (0.04 mmol) was mixed with PCy$_3$ (11.2 mg, 0.04 mmol) and 1,1-diphenyl-2-propynol (4) (8.3 mg, 0.04 mmol) in a solvent of isopropanol-hexane (1:10, 10 ml), and stirred under reflux for 1 hour. Then, NaPF$_6$ (6.7 mg, 0.04 mmol) was added thereto, and further stirred at the room temperature for 12 hours.

The mixture was subjected to filtration, washing with ethanol and hexane, and drying under a reduced pressure, to obtain a recycled, activated catalyst (5a).

The above ring-closing metathesis reaction was carried out with excellent results by using the recycled, activated catalyst (5a), and thus the product was obtained with a yield of 81% by the second use of the catalyst, and with a yield of 98% by the third use.

Example 3

The ring-closing metathesis reaction was carried out in the same manner as Example 2 except for using an activated ruthenium catalyst (5b), which was prepared using the polymer-supported ruthenium complex (3b), instead of the activated ruthenium catalyst (5a).

N-tosyl-2,5-dihydropyrrole was obtained with a yield of 49%.

Then, the recovered catalyst was recycled. The product was obtained with a yield of 72% by the second use of the catalyst, and with a yield of 77% by the third use.

Example 4

The ring-closing metathesis reaction was carried out in the same manner as Example 2 except that a catalyst prepared without $NaPF_6$ was used instead of the activated ruthenium catalyst (5a). N-tosyl-2,5-dihydropyrrole was obtained with a yield of 40%.

The catalyst was recycled. The product was obtained with a yield of 72% by the second use of the catalyst, and with a yield of 77% by the third use.

Example 5

Ring-Closing Metathesis Reaction (RCM)

Various olefin compounds were each reacted in a hexane-toluene (10:1) solvent under reflux for 12 hours in the same manner as Example 2 using 20 mol % of the activated ruthenium catalyst (5a).

The results are shown in the following table.

TABLE 3

| enrty | substrate | product | yield (%) |
|---|---|---|---|
| 1 | allyl-N(Ts)-CH(CO₂Me)-CH₂-CH=CH₂ | N-Ts tetrahydropyridine-CO₂Me | 98 |
| 2 | allyl-N(Ts)-CH₂CH₂-CH=CH₂ | N-Ts tetrahydropyridine | 92 |
| 3 | diallyl-C(CO₂Et)₂ | cyclopentene-C(CO₂Et)₂ | 72 |
| 4 | allyl-O-CH(Ph)-CH=CH₂ | 2-phenyl-2,5-dihydrofuran | 66 |

TABLE 3-continued

| enrty | substrate | product | yield (%) |
|---|---|---|---|
| 5 | methacryl-N(Ts)-allyl | 3-methyl-N-Ts-1,5-dihydropyrrol-2-one | 82 |

Characteristic values of the products are as follows.

TABLE 4

Methyl(DL)-N-Tosyl-4,5-didehydropipecolate. $^1$H NMR δ=2.42(s, 3H), 2.52-2.57(m, 2H), 3.49(s, 3H), 3.78-3.90(s, 1H), 4.02-4.16(m, 1H), 4.87(t, 1H, J=4.3Hz), 5.58-5.70(m, 2H), 7.29(d, 2H, J=8.3Hz), 7.68(d, 2H, J=8.3Hz); $^{13}$C NMR δ=21.4, 27.7, 42.0, 52.0, 52.5, 122.2, 123.3, 127.1, 129.4, 136.1, 143.3, 170.8.
N-Tosyl-1,2,3,6-tetrahydropyridine. $^1$H NMR δ=2.18-2.24(m, 2H), 2.43(s, 3H), 3.17(t, 2H, J=5.7Hz), 3.57(t, 2H, J=2.6Hz), 5.57-5.66(m, 1H), 5.71-5.80(m, 1H), 7.32(d, 2H, J=8.1Hz), 7.67(d, 2H, J=8.1Hz); $^{13}$C NMR δ=21.5, 25.2, 42.6, 44.7, 122.7, 125.0, 127.6, 130.0, 133.2, 143.4.
Diethyl 3-cyclopentene-1,1-dicarboxylate. $^1$H NMR δ=1.16(t, 6H, J=7.1Hz), 3.01(s, 4H), 4.20(q, 4H, J=7.1Hz), 5.61(s, 2H); $^{13}$C NMR δ=14.0, 40.8, 58.8, 61.5, 127.8, 172.2.
2-Phenyl-2,5-dihydrofuran. $^1$H NMR δ=4.77(dddd, 1H, J=1.7, 2.4, 4.1, 12.9Hz), 4.88(ddt, 1H, J=2.0, 6.1, 12.9Hz), 5.77-5.82(m, 1H), 5.87-5.92(m, 1H), 6.02-6.06(m, 1H), 7.65-7.38(m, 5H); $^{13}$C NMR δ=75.8, 87.9, 126.4, 126.6, 127.8, 128.5, 129.9, 142.0.
3-Methyl-N-tosyl-1,5-dihydropyrrol-2-one. $^1$H NMR δ=1.79-1.84(m, 3H), 2.43(s, 3H), 4.33-4.38(m, 2H), 6.85-6.90(m, 1H), 7.33(d, 2H, J=8.3Hz), 7.96(d, 2H, J=8.3Hz); $^{13}$C NMR δ=10.8, 21.6, 50.1, 127.9, 129.7, 134.9, 135.3, 139.2, 145.0, 169.2.

Example 6

An 8-membered heterocyclic compound was obtained with a yield of 57% by ring-closing metathesis in the same manner as Example 5 except that the reaction time was 24 hours, in accordance with the following formula.

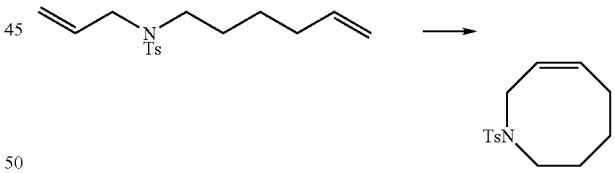

Example 7

Reduction of Carbonyl Group

A reduction reaction of acetophenone was carried out in accordance with the following reaction formula.

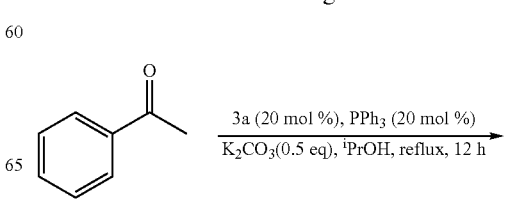

-continued

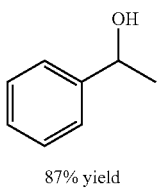

87% yield

Specifically, the polymer-supported arene-ruthenium complex PS-RuCl$_2$(PPh$_3$) (3a) (44.3 mg, 0.17 mmol) produced in Example 1, K$_2$CO$_3$ (58.1 mg, 0.42 mmol), and triphenylphosphine (44.3 mg, 0.17 mmol) were added to and mixed with an isopropanol solution (8.4 ml) of acetophenone (101.4 mg, 0.84 mmol) at room temperature, and then stirred under reflux for 12 hours.

The catalyst was isolated by filtration and washed with ethanol and hexane, and the filtrate was concentrated under a reduced pressure and purified by a silica gel chromatography to obtain 1-phenylethanol (89.3 mg, 87% yield).

Characteristic values of the product are as follows.

TABLE 5

1-Phenylethanol. $^1$H NMR δ=1.46(d, 3H, J=6.4Hz), 2.20(s, 1H), 4.84(q, 1H, J=6.4Hz), 7.20-7.37(m, 5H); $^{13}$C NMR δ=25.1, 70.3, 125.3, 127.4, 128.4, 145.8.

Various ketone compounds and aldehyde compounds other than acetophenone were each reduced in the same manner, so that corresponding alcohol compounds were obtained with a high yield of 60 to 90%.

Example 8

Cyclization of Alkyne Compound

A cyclization/addition reaction of an alkyne was carried out in accordance with the following reaction formula.

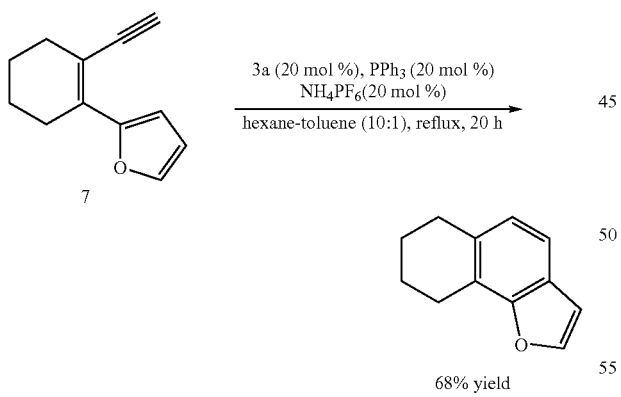

68% yield

Specifically, the polymer-supported arene-ruthenium complex PS-RuCl$_2$(PPh$_3$) (3a) (0.058 mmol/g, 689 mg, 0.04 mmol) produced in Example 1, triphenylphosphine (10.5 mg, 0.04 mmol), and NH$_4$PF$_6$ (6.5 mg, 0.04 mmol) were mixed with 10 ml of a 10/1 hexane-toluene solution of 2-ethynyl-1-(2-furyl)cyclohexene (7) (34.3 mg, 0.20 mmol) at the room temperature, and stirred under reflux for 20 hours.

The catalyst was isolated by filtration and washed with ethanol and hexane, and the filtrate was concentrated under a reduced pressure and purified by silica gel chromatography to obtain 6,7,8,9-tetrahydronaphtho[1,2-6]furan (23.4 mg, 68% yield).

Characteristic values of the product are as follows.

TABLE 6

6,7,8,9-Tetrahydronaphtho[1,2-b]furan. $^1$H NMR δ=1.76-1.79(m, 4H), 2.87(t, 2H, J=5.6Hz), 2.98(t, 2H, J=5.6Hz), 6.70(d, 1H, J=2.0Hz), 6.97(d, 1H, J=7.9Hz), 7.32(d, 1H, J=7.9Hz), 7.56(d, 1H, J=2.0Hz). $^{13}$C NMR δ=22.4, 22.7, 23.3, 106.6, 117.8, 121.1, 124.1, 133.3, 144.0, 153.7.

INDUSTRIAL APPLICABILITY

As described in detail above, according to the present invention, there are provided a novel polymer-supported arene-ruthenium complex and a catalyst thereof, which can be produced by a simple process, are stable and easy to recover, have a high catalytic activity, and can be used for various organic synthesis reactions. There are also provided novel methods for organic synthesis reactions such as ring-opening metathesis reaction of an olefin compound and reduction of a carbonyl group, using the catalyst.

The invention claimed is:

1. An arene-ruthenium complex wherein the complex is represented by the following formula:

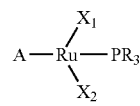

wherein A represents an organic polymer with a side chain, which is an aromatic ring coordinated to Ru, X$_1$ and X$_2$ represent the same or different halogen atoms, and R represents a hydrocarbon group that may have a substituent.

2. The arene-ruthenium complex of claim 1, wherein the hydrocarbon group is an alicyclic hydrocarbon group or an aromatic hydrocarbon group.

3. The arene-ruthenium complex of claim 1, wherein the aromatic ring of the side chain is a benzene ring.

4. The arene-ruthenium complex claim 1, wherein the organic polymer is a polystyrene.

5. A method for producing the arene-ruthenium complex of claim 1, comprising a ligand exchange of a complex monomer represented by the following formula:

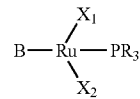

wherein B represents an aromatic compound, which is an aromatic ring coordinated to Ru, and X$_1$, X$_2$ and R are as defined above, with an organic polymer A with a side chain which is an aromatic ring.

6. An arene-ruthenium catalyst for an organic synthesis reaction, comprising the arene-ruthenium complex of claim 1 as an active component.

7. The arene-ruthenium catalyst of claim 6, wherein the catalyst is prepared by mixing the complex with a phosphine compound.

8. The arene-ruthenium catalyst of claim 7, wherein the catalyst is prepared by being mixed with $MPF_6$, in which M represents a monovalent cation.

9. The arene-ruthenium catalyst of claim 8, wherein the catalyst is prepared by being mixed with an alkynyl alcohol compound.

10. A method of an organic synthesis reaction, wherein a ring-closing metathesis reaction of an olefin compound wherein the reaction is carried out in the presence of the catalyst of claim 6.

11. A method of reduction of a ketone or aldehyde compound, wherein the reaction is carried out in the presence of the catalyst of claim 6, to synthesize an alcohol compound.

12. A method of cyclization/addition reaction of an alkyne, wherein the reaction is carried out in the presence of the catalyst of claim 6.

* * * * *